United States Patent
Caufield et al.

(10) Patent No.: US 7,745,115 B2
(45) Date of Patent: Jun. 29, 2010

(54) METHOD FOR THE SURVEILLANCE FOR BIOLOGICAL, CHEMICAL AND RADIOLOGICAL AGENTS

(75) Inventors: Page W. Caufield, New York, NY (US); Deepak Saxena, New York, NY (US); Michael C. Alfano, New York, NY (US)

(73) Assignee: New York University, New York, NY (US)

( * ) Notice: Subject to any disclaimer, the term of this patent is extended or adjusted under 35 U.S.C. 154(b) by 362 days.

(21) Appl. No.: 10/817,102

(22) Filed: Apr. 1, 2004

(65) Prior Publication Data

US 2010/0136586 A1 Jun. 3, 2010

Related U.S. Application Data

(60) Provisional application No. 60/459,941, filed on Apr. 2, 2003.

(51) Int. Cl.
*C12Q 1/68* (2006.01)
*G01N 33/554* (2006.01)
*C12N 1/20* (2006.01)

(52) U.S. Cl. .................. 435/6; 435/7.32; 435/252.5

(58) Field of Classification Search ............ None
See application file for complete search history.

(56) References Cited

U.S. PATENT DOCUMENTS 6,613,571 B2 * 9/2003 Cordery et al. ............... 436/48

OTHER PUBLICATIONS

Manasherob et al., "Germination, Growth, and Sporulation of *B. thuringiensis* subsp. israelensis in Excreted Food Vacuoles of the Protozoan *Tetrahymena pyriformis*", App. Environ. Microbio., May 1998, pp. 1750-1758.*

Hoffmaster et al. "Evaluation and Validation of Real-time PCR Assay for Rapid Identification of *B. anthracis* ", Emerging Infectious Diseases, Oct. 2002, vol. 8, No. 10, pp. 1-12.*

Schlimme et al. (App. Environ. Micro. Jun. 1999, pp. 2754-2757).*

Weinbauer (App. Environ. Micro. Oct. 1998, pp. 3776-3783).*

Agrawal et al. (Current Science 2002, vol. 83, pp. 697-699).*

German et al. Water Science and Technology, 2002, vol. 46, pp. 191-198.*

Manz (Microbiology, 1995, vol. 141, pp. 29-39).*

Eisenman (App Environ Microbio, 1998, vol. 64, No. 4, pp. 1264-1269).*

Barak et al., Bioencapsulation and delivery to mosquito larvae of *Bacillus thruingiensis* H14 toxicity by *Tetrahymena pyrifomis* , J. Invertebr. Pathol. 58(3):455-457 (1991).

Barak et al., Protozoan—enhanced toxicity of *Bacillus thunngiensis var. israelensis* delta-endotoxin against Aedes aegypti larvae, J. Invertebr. Pathol. 63:244-248 (1994).

Butler et al., Collaboration Between Public Health and Law Enforcement: New Paradigms and Partnerships for Bioterrorism Response and Planning, Emerg. Infec. Disease, 8(10):1152-1156 (2002).

Saxena et al., A UV Tolerant Mutant of *Bacillus thuringiensis* subsp. *kursteki* Producing Melanin, Current Microbiology, 44:25-30, (2002).

* cited by examiner

*Primary Examiner*—Sarae Bausch
(74) *Attorney, Agent, or Firm*—Fish & Richardson P.C.

(57) ABSTRACT

Provided is a method of surveillance for hazardous materials, e.g., chemical, biological and radiological agents. The method comprises assaying a sample derived from materials collected from a sample domain for the presence of a chemical, biological, or radiological agent. The sample domain comprises at least one collection point from which the materials are collected in a pre-existing operation unrelated to surveillance.

5 Claims, 1 Drawing Sheet

Figure 1: Surveillance System
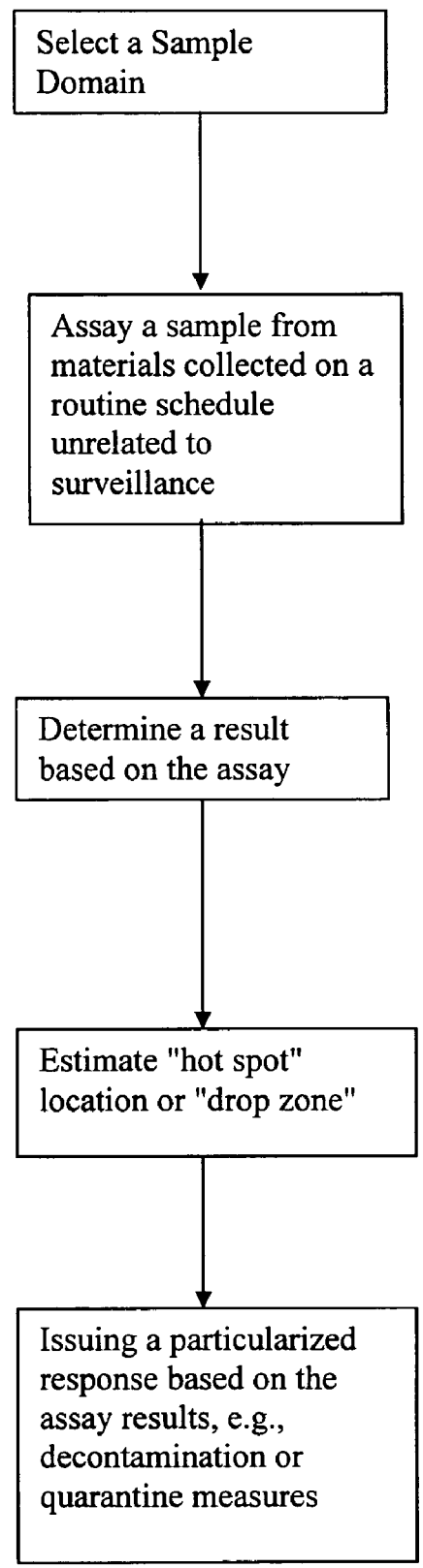

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: PCR primer

<400> SEQUENCE: 1
gatggaggta acccatggag gaa                                              23

<210> SEQ ID NO 2
<211> LENGTH: 28
<212> TYPE: DNA
<213> ORGANISM: Artificial Sequence
<220> FEATURE:
<223> OTHER INFORMATION: PCR primer

<400> SEQUENCE: 2
ctggagctca mtcmactaaa ttggatac                                         28

<210> SEQ ID NO 3
<211> LENGTH: 22
<212> TYPE: DNA
<213> ORGANISM: Artificial Sequence
<220> FEATURE:
<223> OTHER INFORMATION: PCR primer

<400> SEQUENCE: 3
catgattcat gggcagataa ac                                               22

<210> SEQ ID NO 4
<211> LENGTH: 23
<212> TYPE: DNA
<213> ORGANISM: Artificial Sequence
<220> FEATURE:
<223> OTHER INFORMATION: PCR primer

<400> SEQUENCE: 4
ttgtgacact tctgcttccc att                                              23

<210> SEQ ID NO 5
<211> LENGTH: 32
<212> TYPE: DNA
<213> ORGANISM: Artificial Sequence
<220> FEATURE:
<223> OTHER INFORMATION: PCR primer

<400> SEQUENCE: 5
ccggaattcg tttagtactt tcaggggtgt ct                                    32
```

```
<210> SEQ ID NO 6
<211> LENGTH: 33
<212> TYPE: DNA
<213> ORGANISM: Artificial Sequence
<220> FEATURE:
<223> OTHER INFORMATION: PCR primer

<400> SEQUENCE: 6
ccgtgagctc ctgcagtgcg gatscggttg tta                                    33
```

METHOD FOR THE SURVEILLANCE FOR BIOLOGICAL, CHEMICAL AND RADIOLOGICAL AGENTS

This application claims priority under 35 U.S.C. § 119(e) to provisional application No. 60/459,941, filed Apr. 2, 2003, which is incorporated by reference.

FIELD OF THE INVENTION

The present invention relates generally to monitoring for the presence of potentially harmful agents released as an act of terrorism, or by accident, e.g., for homeland security and safety monitoring.

BACKGROUND OF THE INVENTION

Early detection and pre-symptom detection of hazardous materials from a terrorist attack on an area can profoundly alter the outcome of such an attack in terms of morbidity and mortality. This is especially true in cases of high population density. Central to early detection is devising a method to routinely sample spaces in which large numbers of people gather or traverse. For example, in a city such as New York, these spaces include the streets, parks, subways, airports, places of work, and landmarks associated with tourism. During these uncertain times, there is a need for periodic, sensitive and specific surveillance with a high predictive value, which is capable of localizing the epicenter of a biological, chemical, or nuclear attack.

Various sampling methods are known, including wet swabs, wipes, and vacuum and forced air sampling methods. See, e.g., Teshale, E. H. et al., Emergency Sampling for Spores of *Bacillus anthracis*, Emer. Infec. Dis., Vol. 8, No. 10. During the 1991 Gulf War, the U.S. and allied armies tested several different methods for detecting biological, chemical, and radiological agents. These tests are generally not publicly available. Until now, no "macro" method has been proposed for surveillance of streets, walkways, and other public areas where people gather.

U.S. Published Patent Application 2002/0193967 ('967) discloses a method that collects information relating to self-diagnosis and self-medication. In contrast, the present invention monitors the underlying agent(s) that cause the illnesses relied upon by the '967 method, providing a more proactive approach.

U.S. Published Patent Application 2002/0169386 discloses dual monitoring/measurement devices equipped with behavioral chronopharmacological transdermal delivery system. The present invention offers a less intrusive surveillance system for metropolitan areas.

As discussed below, there are many references teaching equipment and methods of assaying for targeted agents, i.e., biological, chemical, and/or radiological agents. For example, U.S. Published Patent Application 2002/0197631 discloses a multi-chambered device for processing biological samples. U.S. Published Patent Application 2002/0168657 discloses a rare event detection system, wherein samples are exposed to or labeled with fluorophores emitting photons at certain wavelengths. U.S. Published Patent Application 2002/0081569 discloses methods and reagents for rapid identification of particles in a liquid sample. The person skilled in the art will quickly realize various combinations, like the inventions mentioned above, references mentioned below, and analogous art, that can be used in accordance with the present invention. However, there remains a need for a cost-effective, systematic approach for detecting the presence of hazardous materials that are being prepared for release or that have been released. Such a method could also provide an early warning of an accidental release, e.g., of radioactive materials from a nuclear energy plant.

SUMMARY OF THE INVENTION

Provided is a method of surveillance for hazardous materials, e.g., chemical, biological and radiological agents. The method comprises selecting a sample domain; obtaining a sample from the sample domain; and assaying the sample for the presence of a chemical, biological, or radiological agent. The sample domain may be an area designated for collection of materials collected for other reasons, e.g., normal waste collection services. In alternative embodiments the collection occurs on a more systematic basis, e.g., through a predetermined, traceable routes. The predetermined traceable routes may converge on a centralized location.

In an alternative embodiment, the sample consists of debris or fluids that result from cleaning or washing out a container or instrumentality used in the collection of materials from the sample domain; determining a result based on the presence or non-presence of a chemical, biological, and radiological agent from the sample; and reporting the result. Again, the collection of materials can be primarily for another purpose, e.g., municipal sanitation.

Still another alternative embodiment involves selecting a sample domain, in which materials are collected on a regular, systematic basis through a predetermined, traceable route, the predetermined traceable route converging on a centralized location; selecting a sample from the sample domain, the sample consisting of debris or fluids that result from cleaning or washing out a container used in the collection of materials from the sample domain; assaying the sample for the presence of a chemical, biological, or radiological agent using, for example, molecular assays, PCR, radiation detector technology, spectrometry, or RIA; determining a result based on the assay, the result indicating the particular agent present in the sample; and reporting the result. The reporting can elicit particularized responses based on the result, such as careful searching of the contaminated area (hot spot) to pinpoint the source of contamination.

Still another alternative embodiment involves the introduction of *Tetrahymena pyriformis* into the environment or the collected material to ingest and concentrate, i.e. bioencapsulate, *Bacillus* spores. *Tetrahymena pyriforms* can also be used in conjunction with other embodiments of the present invention.

Still another alternative embodiment involves use of *Bacillus thuringiensis* strains, including *Bacillus thuringiensis* melanin to serve as a model for *Bacillus anthracis* for testing the surveillance system for the present invention.

A clear advantage results from various embodiments of the present invention—harnessing existing collection services to monitor for hazardous materials, thus obviating the need to create a separate network of collection facilities. Indeed, garbage and trash collection, and street sweeping services, cover every point of urban human habitation. To achieve this degree of coverage with a dedicated sample collection network would require a tremendous expenditure. The present invention renders such expenditures unnecessary.

BRIEF DESCRIPTION OF THE DRAWINGS

FIG. 1 sets forth a flow chart of an embodiment of the surveillance system of the present invention.

DETAILED DESCRIPTION

Embodiments of the present invention take advantage of existing procedures and infrastructures for monitoring for the presence of hazardous materials. In particular, trash, debris, or particulate matter collection in any area, e.g., a county, city or large building (such as an airport, train, or bus terminal), occurs or can occur on a systematic basis. By testing samples from collected trash, it will be possible to locate a region of high concentration of a hazardous agent. Once authorities locate such a region, they can undertake a search to identify the source of the hazardous material. Using this approach greatly increases the monitoring power for these kinds of agents without requiring an investment in a dedicated sample collection infrastructure. It also greatly improves monitoring efficiency, because when searches for hazardous materials need to be conducted, they will focus on an area already identified as "hot".

FIG. 1 sets forth one embodiment of a surveillance system (10). A sample domain is selected. A sample domain is the defined area from which collected materials are obtained on a systematic basis so that the location from which collected materials are obtained can be ascertained or is known. A sample is assayed from materials collected on a routine schedule unrelated to surveillance. A result is determined, indicating the presence, or relative or absolute amount of a targeted agent. Based on the assay results, a hot spot or drop zone is estimated. Once the hot spot is ascertained with a requisite degree of certainty, the surveillance system issues a particularized response based on the assay results, e.g., implementation of decontamination or quarantine measures.

The hazardous materials to be monitored include biological, chemical, and radioactive materials used in weapons. It is highly probable that activities that pose a public threat will involve release of such materials into the local environment, thus contaminating the garbage or trash of the local environment. Such release will likely precede actual delivery of the hazardous materials, since proper containment facilities will likely be unavailable to terrorists when they are preparing or transporting such weapons.

In another embodiment of the present invention, the accidental release of hazardous materials from authorized sources is monitored, such as releases from biomedical research facilities, chemical plants, or nuclear power stations. A positive assay result indicates a safety breach (or unlawful release).

Thus, one embodiment of the invention relates to the ability to monitor for chemical or biological agents. Another embodiment of the invention relates to the ability to monitor for radiological agents. The present invention can monitor possible acts of terrorism or other belligerent acts by NGO's (non-government organizations), nation-stations, or isolated individuals. Another use of the present invention is to monitor errant disposal of radioactive, chemical or biological hazards at businesses and institutions (e.g., testing standard trash dumpsters at various hospitals). Alternative embodiments are directed toward the control of natural outbreaks, such as the West Nile virus.

Definitions

Hazardous materials are entities that may cause deleterious or undesirable effects to a living creature, including death, if inhaled, absorbed, ingested, or otherwise encountered. As used herein, the term hazardous materials also encompasses materials that, although not being deleterious or undesirable per se, serve as models for other hazardous materials (e.g. non-pathogenic *Bacillus thuringiensis* used as a model for *Bacillus anthracis*).

Targeted agent(s) are the particular hazardous material(s) to be detected in samples using various assay techniques, i.e., they are targeted for detection. Mindful of technology to be utilized in accordance with the present invention, targeted agent(s) may comprise all, or substantially all hazardous materials that pose a threat to living creatures.

Chemical agents are substances, generally prepared by chemical synthesis or extraction from natural sources, that may cause deleterious or undesirable effects to a living creature if inhaled, absorbed, ingested, or otherwise encountered. These agents include acute poisons, teratogens, nerve agents (e.g., sarin and VX), carcinogens, blister agents (e.g., mustard gas and lewisite), choking agents (e.g., phosphene), blood agents (e.g., hydrogen cyanide), napalm, and the like. The foregoing list is exemplary and not limiting.

Biological agents include organisms and viruses, or entities synthesized by or derived therefrom, that may cause deleterious or undesirable effects to a living creature if inhaled, absorbed, ingested, or otherwise encountered. These include pathological bacteria (salmonella, plague, anthrax, encephalitis, meningitis, tularemia, and the like), viruses (smallpox, polio, West Nile, Ebola, VHF (Viral Hemorrhagic Fevers) and the like), eukaryotic pathogens (amoeba, *trichinella spiralis*, etc.), toxins or proteins (such as ricin, *botulinum* toxins, or prions) or parasites (such as *Leishmania, trypanosome, filariae, cryptosporidium*, and the like). The foregoing list is exemplary and not limiting. As one of ordinary skill in the art can appreciate, there is an overlap between chemical agents that are natural product extracts and biological agents that are molecules produced by organisms. For purposes, of the present invention, these agents fall into both categories.

Radiological agents include nuclear weapons, and radiological dispersal devices or weapons (e.g., dirty bombs). Any instrumentality that aims to inflict the perils of radiation upon a living entity is considered a radiological agent.

Samples are substances, fluid or solid, obtained from collected material (e.g., by selection, washing, solvent extraction, compression and liquor collection, or any other technique) or otherwise presently or formerly in communication with the collected material. The sample may also consist of the collected material itself (e.g., direct analysis of a piece of paper for hazardous materials).

Collected material includes household or industrial trash or garbage; public trash; yard waste; recyclable products; litter; discarded material; or any other material no longer on an individual's person or stored within that individual's property or designated space. Collected material may also constitute the ambient air or other fluid environment of a particular location.

A sample domain is the defined area from which collected materials are obtained on a systematic basis so that the location from which collected materials are obtained can be ascertained or is known.

When materials are collected in a predetermined, traceable route, the relative order of collections can be ascertained based on an established protocol or pattern.

When materials are collected in a predetermined pattern, the sample domain is known for that day, week, month, or other time interval.

A street sweeper machine is a machine that cleans and/or collects trash from streets, sidewalks, floors, promenades, thoroughfares, depots, or other places where people gather. A street sweeper machine embodies a street sweeper, and analogous apparatuses such as floor buffers, including smaller or modified versions used within buildings such as public transportation terminals.

An assay is a biological, chemical, or physical test of sufficient specificity and sensitivity to detect the presence of target agent(s). The presence of targeted agent(s) may be determined by a "positive" or "negative" test result, or presence may be ascertained by comparison to a normal level. A normal level may include quantified background noise, or determined by comparison with levels of targeted agent(s) from a second sample domain.

Collection integrity is preserved when the samples are collected, maintained, and processed in such a way as to minimize the likelihood of samples being adulterated, discarded, or otherwise manipulated so as to prevent the successful functioning of the surveillance system. Collection integrity can be preserved, for example, by close monitoring of the chain of custody.

Sample Domain

Embodiments of the surveillance system of the present invention utilize existing and routine infrastructure and is thus exportable to any metropolitan area. A sample domain is selected, from within which there is a collection of materials. To facilitate uniform sample preparation, the collected materials may be brought to a central location, i.e., the collection of materials converges on a centralized location. Typically materials are collected in a predetermined pattern, and alternatively, also collected according to a predetermined, traceable route.

In an alternative embodiment of the present invention, materials are collected, and samples are obtained, in a predetermined pattern before converging at a centralized location. This embodiment provides the ability to more quickly and accurately ascertain the exact location of a hot spot from within the area encompassed by the sample domain. Thus a predetermined pattern does not necessarily involve material collection for testing at a centralized point. Even if sample collection occurs at a centralized point, knowledge of the pattern or route of collection permits correlation of a concentration gradient of the targeted agent with the pattern or route to localize a hot spot within the sample domain. Hot spots can also be located by other means known to those of ordinary skill in the art.

Various means of collecting the materials are within the scope of the present invention, including street sweeping machines, push carts (as used in railroad/bus terminals, airport terminals, and large building complexes), yard waste collection, recycling efforts, and industrial vacuum trucks. Stationary units, in which material from a specific area or route is collected, may also be used. These stationary units include waste receptacles, recycling bins, and sewer grates.

Routine collection of materials in the sample domain in accordance with the present invention provides a great advantage over having to make visits to many sites for the sole purpose of monitoring. Incorporating sampling techniques as part of a pre-existing operation provides savings for the municipality, and thus, the taxpayer.

There are various situations within the scope of the present invention in which environmental sampling can take advantage of various synergies, including the centralized collection of debris from areas where large numbers of people traverse, and/or utilizing existing infrastructure. For example, samples can be taken from any final or intermediate collection point along a municipal or private trash route. Containers collecting trash from buildings, subways, and thoroughfares can be included in the early warning surveillance system. Air sampling, particularly from a centralized point, such as normal filters at intake or vent areas of a ventilation system, can be useful in sampling confined spaces, such as public buildings and subways, and is within the scope of the present invention. Again, the notion of centralized collection points, regardless of the method of collection, greatly reduces the workload and takes advantage of existing infrastructure.

Washing and Sample Isolation

The sample, selected from the sample domain, should be in a medium that would contain targeted agent(s), if these targeted agent(s) are present. Oftentimes, it will be desirable to obtain a liquid sample. Such a sample can be obtained by taking an aliquot from an exiting liquid stream from a washing step. The person of ordinary skill will quickly realize that according to the present invention, one could wash an instrumentality, or obtain a liquid sample from the instrumentality itself, that is somehow involved in the centralized collection of debris from areas where large numbers of people traverse.

The washing step, for example, can involve the washing of the mechanical machinery involved in the collection process. In one embodiment of the invention, street sweeper machines' brushes or collection bins are rinsed. An aliquot is taken from an exit stream of the water discharged from the rinsing of the brushes or collection bins. This aliquot could contain targeted agent(s), e.g., anthrax spores.

In areas where such washing regularly occurs, or in areas in communication with liquids collected from the predetermined pattern, commercially available automatic sampling devices can be installed (e.g., Hoskin Scientific, Vancouver, BC). In this manner, samples can be isolated with minimal manpower and community resources.

In an alternative embodiment, the analyzed sample is drawn from water or other liquid solution, e.g. a cleaning solution, that is in communication with the collected materials. For example, a sample can be obtained from a liquid medium used in the collection of debris, e.g. obtaining samples from a liquid cleaning solution that is recycled through floor-cleaning machines. Thus, the sampled water can interact directly with the collected materials, or interact with structures that once contained, or currently contain the collected materials. For example, trash containers could be rinsed as they are dumped, and the rinse could be analyzed for the presence of hazardous chemical or biological agents. The present invention, however, is not limited to water sampling. According to the present invention, any fluid or solid can be analyzed depending on the targeted agent to be monitored and assay technique chosen to determine the presence of the agent.

A washing step may be suitable to obtain a sample in a proper medium, based on various factors, including convenience, the solvent power of the liquid used in the washing operation, the ability of the liquid to entrain, encapsulate, or otherwise be in communication with the targeted agent(s), or the particular assaying technique. In other embodiments of the invention, the targeted agent(s) is already in a proper medium, and a washing step, or any other similar method known to the skilled artisan, is not required.

Furthermore, advancements in assaying technology allow for the monitoring of hazardous agent(s), including biological agents, using a device small enough to be hand-held. These devices can be placed in communication with a collection bin. Using such technology, samples can be scanned as collected materials enter, for example, the storage mechanism in street sweepers. Furthermore, collected material can be scanned as they enter conventional collection bins, e.g., dumpsters, or as these materials enter trash compactors. Such technology, used in accordance with the present invention, eliminates the need for both dedicated sample collection and off-site assaying.

Assaying Techniques

Although not limited by a particular assaying technique, the detection of chemical, biological, or nuclear agents is vital to the successful operation of the present invention. The measure of how well this detection is accomplished is statistically defined as specificity, sensitivity, and positive predictive value. Detection assays need to be sufficiently reliable and sensitive to reduce false positive and false negative rates to an acceptable level, and be capable of examining samples for a range of likely agents used in an attack. Embodiments of the present invention may involve more than one method of environmental sampling.

Embodiments of the present invention employ real time PCR techniques, a method which can be extremely sensitive and specific. Such methods rely upon the detection of signature DNA or RNA, i.e. unique fragments of DNA or RNA found in the targeted agent. Samples from the environment can be treated to remove substances that interfere with the assay. Obtaining DNA or RNA free of clays and inhibitors will improve the ability to identify DNA from samples potentially containing harmful agents. Methods that remove or neutralize PCR-inhibiting contaminants may be used by the skilled artisan in accordance with the present invention. For example, the sample can be treated with antibiotics, such as polymyxin, to exclude contaminants and provide a sample enriched with the targeted agent, if present.

An example of an inhibitor to real time PCR and other assay techniques are biological materials that are not a result of a rare event, such as a terrorist incident or an industrial accident. For example, collected material such as feces, food, and animal remains may yield considerable amounts of bacteria, and the presence of such material should not hinder efforts to identify harmful agents, such as anthrax. Further, soils, detergents and a wide assortment of chemicals can interfere with the isolation and purification of DNA or RNA. Embodiments of the present invention provide gathering and concentrating techniques (e.g. bioencapsulation) for isolating and/or amplifying a hazardous agent from within a sample, or more generally, from within a sample domain. Such efforts allow targeted agents to be distinguished from large sources of background noise and inhibitors which may interfere with the isolation and purification of DNA or RNA.

As it is unlikely that any single system will be 100% sensitive and specific, especially given the nature of the background contamination and biological diversity of other environmental bacteria, fungi and viruses, most of which have yet to be identified, the invention also contemplates using two or more different analytical methods to identify targeted biological agent(s), such as immunoassay and PCR for a biological hazard. Single assays, such as mass spectrometry, may be sufficient for a chemical or radiological hazard.

After isolating a sample, obtained by methods generally known, including washing, the sample may be subjected to further processing and analysis. As explained in Published U.S. Patent Application 2002/0197631, hereby incorporated by reference in its entirety, processing of such samples may involve one or more of the following: homogenization of biological tissues, lysis of cells, suspension or dissolution of solid particulates, liquefaction of solid material, or other methods that enrich the targeted agent(s). Often, such sample preparation also entails extensive enzymatic digestion, the use of chemical reagents, and/or mechanical disruption. Samples can also be processed using techniques such as distillation, use of detergents, solubilizing, or polar and apolar extraction. Polymerase chain reaction (PCR) or gel electrophoresis can be used to purify or amplify target agent(s), such as nucleic acid sequences and/or proteins in a sample. The purpose of such processing is to obtain a sample in which targeted agent(s), assuming their presence, would be sufficiently concentrated for the chosen assaying technique. After processing, samples are typically subjected to an analytical and/or detection procedure. See e.g. U.S. Pat. No. 5,968,515, hereby incorporated by reference.

Assaying for Chemical Agents

The presence of chemical agents in collected samples is determined by methods known to those skilled in the art. As explained above, to improve the detectability of any targeted agent(s), the skilled artisan will employ techniques to obtain a sample in a condition to be accurately and easily assayed, e.g., a sufficiently concentrated sample. Also, chemical derivatization can be performed to introduce a chromaphore to the targeted agent(s), if present. Further, removal of interfering substances, through the use of chromatographic separations for instance, may enhance the dectability of the targeted agent(s).

One embodiment of the present invention employs spectrometry technology to determine the presence of a targeted agent(s) on the basis of the amount of visible or ultra-violet light absorbed by the sample. See, e.g., Mathews van Holde, Biochemistry (Benjamin/Cummings Publishing Co., Inc.) 205-212 (1990). Similarly, spectrometry technology can determine the presence of a targeted agent(s) on the basis of radiation absorbed by the sample.

Another technique to determine the presence of targeted agent(s) is mass spectrometry. Mass spectrometry, which can be utilized as a service from, e.g., Sequenom, Inc., is an analytical technique for determining the composition of compounds present in a sample. In a single stage mass spectrometer using a quadrupole mass filter, compounds in a sample are ionized, accelerated and focused to form a stream or beam of ions that enters a first quadrupole mass filter. Appropriate adjustment of the alternating and constant voltages applied to the first or only quadrupole mass filter allows the user to select which ionic species are transmitted through the filter. Ions emerging from the filter are detected and converted to electrical impulses or current by known means such as an electron multiplier. Rapid scanning of these voltages further allows the user to produce a spectrum of the ionic species corresponding to the sample compounds.

One skilled in the art can obtain molecular information via mass spectrometry to determine the presence and/or relative levels of targeted agent(s), assisted by various spectral interpretation methods and database searching tools. Examples of some of these methods and tools can be found at the Swiss Institute of Bioinformatics website, and the European Molecular Biology Laboratory website. Examples of a mass spectrometer apparatus can be found in U.S. Pat. No. 6,525,314.

Also, with knowledge of the tendency of targeted agent(s) to precipitate when placed in communication with a reagent, the presence or non-presence of a targeted agent(s) can be ascertained, and the relative amounts of the targeted agent(s) can be quantified using gravimetric analysis techniques known to those skilled in the art.

High Performance Liquid Chromatography (HPLC) can also be used to ascertain the presence of hazardous chemical agents. As explained in U.S. Pat. No. 4,565,787, HPLC can be employed with a reverse phase column to achieve detection of chemical agents based on ultraviolet/visible absorption of fluorescence. Other chromatographic supports can also be used for HPLC analysis. Alternatively, gas phase chromatography, alone or in combination with mass spectrometry, can be used. Such techniques can be used to detect hazardous chemical agents (e.g., sulphur mustards).

Assaying for Biological Agents

Hazardous biological agents include microbial organisms, viruses, or entities synthesized by or derived therefrom, that may cause deleterious or undesirable effects to a living creature if inhaled, absorbed, ingested, or otherwise encountered. Biological agents may be introduced by a person wishing ill-will, or alternatively may be the result of natural outbreaks or diseases. In this latter regard, attention is drawn to disclosures such as U.S. Pat. No. 6,372,424, which describes methods for the detection and identification of bacterial and viral pathogens in a sample.

Successful detection of microbial agents can involve distinct stages: the sample preparation and processing to obtain template DNA, the amplification of specific signature segments of DNA using template specific DNA primers and probes, and detection of resulting, selectively amplified DNA product.

Sample preparation methods yield DNA from environmental samples obtained from debris collection facilities. The skilled artisan will appreciate that various techniques exist for obtaining suitable DNA samples that work within the scope of the present invention. Numerous methods have been published, some as simple as boiling samples. Furthermore, the amplification of specific segments unique to a specific microbe can be accomplished using polymerase chain reactions (PCR). See, e.g., U.S. Pat. Nos. 4,683,195, 4,683,202, 4,965,188, 4,800,159 and 6,287,769, which are hereby incorporated by reference.

The wide variety of known and future-developed biological agents renders detection efforts challenging. Nonetheless, specificity can be obtained with a high degree certainty given that the most likely agents of bioterrorism have unique segments of DNA that can be detected from very small amounts of sample. For example, specific primers and probes are commercially available for *Bacillus anthracis* (IDI, Quebec, Canada).

One embodiment of the present invention involves the use of a carrier to replicate, gather, and/or concentrate biological agents, chemical agents, or other hazardous materials, e.g. viruses. For example, polymers, such as poly(glyceryl silicilate), can be used to encapsulate functional proteins, as disclosed in U.S. Published Patent Application No. 2004/0034203; U.S. Published Patent application No. 2004/0046963; Gill, I. et al., "Bioencapsulation within synthetic polymers (Part 2): non-sol gel protein polymer biocomposites", Trends in Biotechnology, 18:469-479 (2000); and LeJeune, K. et al., "Covalent Binding of a Nerve Agent Hydrolysing Enzyme within polyurethane foams", Biotechnology and Bioengineering; 51, 450-457 (1996), each of which is hereby incorporated by reference. Furthermore, organisms, such as protozoa, serve as a bioencapsulation systems to gather and concentrate the targeted agents. Such efforts increase the relative amount of, and/or isolate unique DNA and RNA segments, thereby providing easier detection.

Higher life forms can also serve as carriers, which can be introduced and/or isolated from the collected materials in order to concentrate the targeted agent. For example, mosquitoes and birds are carriers for the West Nile Virus; the West Nile Virus replicates from within these carriers. According to embodiments of the present invention, conditions favorable to the use of such carriers are promoted and/or utilized to maximize the presence of such targets within the sample domain of the present invention. For example bug spray operations may be scheduled in conjunction with street sweeping activities to maximize the collection of carriers within the sample domain. The carrier may be added to the collected materials, or may be already present, and isolated from the collected materials.

Before introducing the carrier (e.g. a protozoa to bioencapsulate a targeted agent), liquid samples can be first processed to isolate particles of the same general size as the targeted agent. This could be accomplished by removing relatively larger particles with a filter having a pore size larger than the targeted agent, and subsequently accumulating the target agent as part of a filtrate remaining on a membrane having a pore size smaller than the targeted agent. The sample can be introduced to the membranes by, for example, suction filtration. Other methods to isolate portions of the sample containing the targeted agent based on size will present themselves to those of ordinary skill in the art.

The carrier, if not already found within the sample domain, can be introduced to the sample under conditions favorable to amplification. For example, the sample can introduced to a saline solution, such as Ringers solution, prior to receiving the carrier.

The sample can be further treated to optimize the efficiency of the carrier used to bioencapsulate, or otherwise amplify DNA from the targeted agent. For example, the sample can be treated to remove agents which prevent the carrier from amplifying the targeted agent. Further, when using bioencapsulation techniques, the collected sample can be treated to remove materials besides the targeted agents that are favored by the carrier, e.g. removing bacteria which is preferred by the encapsulating mechanism over the targeted agent. Removal of barriers to the carrier's ability to concentrate the targeted agent can be effected by, for example, heating the sample, treating the sample with an anti-bacterial agent, by changing the conditions of the sample to provide a favorable environment for the carrier to bioencapsulate or otherwise concentrate the targeted agent, e.g. by introducing a buffer to control the pH, or by selecting carriers based on a greater affinity for the target microorganism.

In one embodiment of the invention, the protozoa *Tetrahymena pyriformis* is introduced to a sample in order to bioencapsulate spores of *Bacillus*, e.g. *Bacillus anthracis*, from the sample. In an alternative embodiment, *Tetrahymena pyriformis* introduced to a sample in order to bioencapsulate spores of *Bacillus thuringiensis*, which is used as a non-pathogenic surrogate of *Bacillus anthracis* to test and implement the surveillance system of the present invention. *Tetrahymena pyriformas* can be commercially obtained from Carolina Biological Supply Company (Burlington, N.C.). The publications Z. Barak et al., "Bioencapsulation and delivery to mosquito larvae of *Bacillus thuringiensis* H14 toxicity by *Tetrahymena pyriformis*, J. Invertebrate Pathol., 58(3):455-57 (November 1991); Z. Barak et al., "Protozoan-enhanced toxicity of *Bacillus thuringiensis* var. *israelensis* delta-endotoxin against Aedes aegypti larvae" *J. Invertebrate Pathol.*, 63(3):244-248 (May 1994); Manasherob et al., Germination, Growth, and Sporulation of *Bacillus thuringiensis* subsp. *israelensis* in excreted food vacuoles of the protozoan *Tetrahymena pyriformis*, Appl. Environ. Microbiol., 64(5): 1750-1758 (May 1998); Manasherob et al., Raising activity of *Bacillus thruingiensis* var *israelensis* against *Anopheles stephensi* larvae by encapsulation in *Tetrahymena pyriformis*, (Hymenostomatida:Tetrahymenidae) J. Am. Mosq. Control Assoc. 12(4):627-31 (December 1996); Ben-Dov et al., Spores of *Bacillus thuringiensis serovar israelensis* as tracers for ingestion rates by *Tetrahymena pyriformis*, J. Invertebr. Pathol. 63(2):220-222 (March 1994); Zaritsky et al., Digestibility by and pathogenicity of the protozoa *Tetrahymena pyriformis* to larvae of *Aedes aegypti*, J Invertebr. Pathol. 59(3):332-334 (May 1992). Each of these references are hereby incorporated by reference.

In a further application of these embodiments, the sample can be filtered through a heated membrane, e.g. a membrane heated to about 70° C. Heating kills vegetative bacteria, which are also consumed by *Tetrahymena pyriformis*. The presence of such vegetative bacteria in a sample could inhibit the concentration of *Bacillus* species within the *Tetrahymena pyriformis*. The combined filtration-heating process allows exclusion of particles having sizes larger than the pore size of the filter employed, and also eliminates material which interferes with the bioencapsulation of, for example, *Bacillus anthracis*.

In other embodiments, the sample is warmed to a range of about 70-80° C. before the *Tetrahymena pyriformis* is introduced. The sample (e.g. a cell suspension) can be heated for a period of time to kill vegetative bacteria, e.g. 10-20 minutes, rinsed, and suspended in a pure culture medium of, for example, $10^{5-6}$ *Tetrahymena pyriformis*. The *Tetrahymena pyriformis* is allowed to remain in communication with the sample for a time sufficient to bioencapsulate any *Bacillus anthracis* in the sample. In various embodiments of this aspect of the invention, the *Tetrahymena pyriformis* is maintained in communication with the sample for about 60-90 minutes.

In other embodiments, a sample of debris fluid is introduced to two membranes. The first membrane can be heated, and serves to exclude particles having a larger size than the targeted agent, and to kill bacteria, such as vegetative bacteria. The first membrane can have a pore size of, for example, about 0.45-1.2 µm. The second membrane serves to allow particles smaller than the targeted agent to pass through, i.e. the targeted agents remain on the membrane as a filtrate. The second membrane can have a pore size of, for example, about 0.2 µm. The membranes may be rinsed with a sterile physiological saline solution to remove soluble contaminants yet preserve tonicity.

Prior to introducing the *Tetrahymena pyriformis* to the sample, the *Tetrahymena* can be starved in normal saline for a period of time sufficient to maximize affinity for the targeted agents. In one embodiment of the present invention, the *Tetrahymena pyriformis* is starved for about 2-3 hours. *Tetrahymena pyriformis* can be introduced to a sample that has been placed in a solvent favorable to the encapsulation, for example diluted Ringers solution or other saline solvents. Alternatively, the *Tetrahymena pyriformis* can be introduced to the sample in situ.

Vital dyes such as Crystal Violet or Methylene Blue can be added to the sample in situ or in a separate solution with the carrier. This provides selectively stained targeted agents, e.g. *Bacillus anthracis*, which can be visually observed within the protozoan culture medium.

In various embodiments, the *Tetrahymena pyriformis* are harvested before the their vacuoles are secreted, which generally occurs after about 90 minutes of contact with a sample with *Bacillus anthracis* present.

The carrier, e.g. *Tetrahymena pyriformis*, containing concentrated and purified targeted agent, e.g. *Bacillus* spores, can then be gathered via centrifugation, filtration, chemotaxis, or other methods known to those of ordinary skill in the art. The carrier is lysed and processed for the extraction of DNA. In embodiments in which *Bacillus* spores are the targeted agent, and *Tetrahymena pyriformis* is the carrier, DNA is contained on or near their surface layer as a result of the sporulation process. In such embodiments, the samples can be centrifuged, washed, and passed through filters to separate the targeted agents and the carrier. Filter sizes can be determined by the skilled artisan, and can range, for example, from about 0.75 µm to about 1.0 µm.

In various embodiments, DNA primers specific to the targeted agent being surveyed would then be assayed by real time PCR. For example, three genetic loci unique to *Bacillus anthracis* have been recommended by the CDC and primers and reaction conditions are commercially available (e.g. IDI, Quebec, Canada). Techniques recommended by the CDC for assaying for anthrax are disclosed in J. Environ. Health, Anthrax—CDC Review, October 2003; 66(3):42; Butler et al., Collaboration Between Public Health and Law Enforcement: New Paradigms and Partnerships for Bioterrorism Response and Planning, Emerg. Infec. Disease, 8(10):1152-1156 (October 2002); and Hoffmaster A F et al., Evaluation and validation of a real-time polymerase chain reaction assay for rapid identification of *Bacillus anthracis*, Emerg Infect Dis., Vol. 8, October 2002. Each of these references are hereby incorporated by reference in their entirety.

In various embodiments, subsequent detection of unique products of PCR include real time PCR (RTm-PCR) (e.g. Applied Biosystems, Foster City, Calif.; SmartCycler, Sunnyvale, Calif.) and mass spectrometry (e.g., Sequenom, San Diego, Calif.) in which fragments of the end products of PCR are analyzed for size and mass. An alternative method of detection of biological agents involves use of phage-derived enzymes for quantitative and qualitative determination of targeted agent(s). In one embodiment of this third method, phage associated lytic agents are introduced to a disposable test system device, and subsequently analyzed by a luminometer in order to deduce the presence or non-presence of targeted agent(s). See U.S. Pat. No. 6,395,504. To date, however, RTm-PCR stands as the gold standard and was used by the CDC to detect *B. anthracis* spores in the October 2001 mail outbreaks.

According to one embodiment of the invention, samples are gathered from a sample domain described above, DNA extracted, and samples divided into two lots—one for RTm-PCR detection and the other for mass spectrophotometric detection. A third sample could be prepared for phage-enzyme detection. High throughput cyclers can be employed, including robotic staging platforms and 96- and 386-well microtiter plates capable of handling over 2000 samples per day.

In another embodiment of the present invention, the surveillance system utilizes immunoassay, such as radioimmunoassay (RIA), to assay for targeted agent(s). As explained in U.S. Pat. No. 4,656,143, RIA involves radiolabelled analogues of targeted agent(s), which competes in solution during incubation with the targeted agent(s) for binding to an antibody attached to a solid phase. After a suitable predetermined incubation period, the solid phase is removed from the solution, washed, and the amount of radiolabel associated with the solid phase is measured. This gives an inverse measure of the amount of targeted agent(s) in the sample. In an immunoradiometric assay (IRMA) a similar protocol is followed except that a labeled antibody is used to provide a detectable signal. In a particular type of IRMA, commonly known as a "sandwich assay", a solid phase is provided with an antibody capable of binding to a determinant of the targeted agent(s). A second, labeled, antibody to another determinant of the targeted agent(s) is provided in a liquid component. The solid phase and the liquid component are incubated together with the sample suspected to contain analyte. Any analyte present becomes attached to the solid phase and labeled antibody becomes attached to the targeted agent. After incubation the solid phase is separated from the liquid component and the amount of label associated with the solid phase is measured, this giving a direct indication of the presence and amount of targeted agent(s) present.

Individual biological molecules can be detected by immunoassay, chromatography, mass spectrometry, and even biological assays based on responses of cells to the presence of an agent. The latter include reporter gene assays, phototype assays, gene expression profile assays (functional genomes, e.g., on a nucleic acid microarray), and protein expression assays (functional proteomics, e.g., on a two-dimensional gel or microarray).

Assaying for Radiological Agents

Radiological agents include nuclear weapons, and radiological dispersal devices or weapons (i.e., dirty bombs). Any instrumentality that aims to inflict the perils of radiation upon a living entity is considered a radiological agent.

The presence of radiological agents in collected samples is determined by methods known to those skilled in the art. For example, embodiments of the present invention employ alpha, beta, and/or gamma irradiation technology to determine the presence of radiation. Mass spectrometry, which can detect atomic mass characteristic of radioisotopes, can also be used.

As explained in U.S. Pat. No. 4,426,579, apparatuses known in the art as Geiger-Mueller (G-M) tubes can be used to detect radiation in accordance with the present invention. As the skilled artisan will appreciate, Geiger-Mueller tubes produce a pulse of electrons, derived from a photon, that impinge upon a cathode inside the G-M tube. Due to their interaction with other atoms in the tube, the G-M pulses generate a random pulse train having an average repetition rate which ultimately provides a measure of radiation intensity according to relationships known in the art. Other detection techniques for radioisotopes include, but are not limited to, scintillation testing and x-ray film exposure.

Analyzing Results and Subsequent Actions

It should be understood that assaying a sample derived from materials collected from a sample domain for the presence of a chemical, biological, or radiological agent may involve comparison to normal levels of the targeted agent(s), i.e., background noise. In other words, determining the presence of targeted agent(s) need not be an all or nothing proposition. To draw an analogy to the electrical arts, determining the presence of a targeted agents may be thought of as an analog process in certain embodiments, as opposed to strictly a digital process.

For example, there are normally minute amounts of *Bacillus anthracis* present in the environment from biological sources such as animal waste, farm products, or other organic matter. An assay indicating the presence of such infinitesimal amounts is not indicative of a terrorist attack, as this background noise will usually be present. In such circumstances, one may first ascertain "normal" levels of a targeted agent, such as *Bacillus anthracis*, and then compare these levels to the current output, before determining the presence of a chemical, biological, or radiological agent. In the event of a terrorist attack, one can expect at least a two-fold or greater increase in the current assay results, as compared to normal, background noise.

It may be impractical or impossible to quantify background noise. For example, upon the introduction of an assay for a new targeted agent, data may not exist to sufficiently state what level of the targeted agent is normal. Under these circumstances, it may be useful to compare the output from various sample domains within a municipality, or better yet, sample domains from geographically diverse areas. Even without knowledge of what amounts of the targeted agents is normal, one can still determine the presence of chemical, biological, or radiological agent by noting a relatively large signal in an assay result from a particular area, as compared to other sample domains that have similar characteristics. In other words, detecting a contamination gradient provides evidence of an abnormal situation.

Furthermore, it should be understood that the present invention, which is useful in detecting an increase in levels of targeted agent(s) relative to the results of an earlier assay, may also be employed to detect a decrease in the level of targeted agent(s) relative to the results of an earlier assay. For example, samples collected via automated trash collection can be used to determine when it is safe to resume normal living arrangements in a sample domain previously designated as unsafe, e.g., the site of a nuclear incident or chemical spill. These sample determinations can be independent of, or adjunctive to, specific assays in the contaminated area for reduction in the amount of targeted material.

Once the particular assaying technique indicates a positive result, either directly or, as discussed immediately above, indirectly, the exact location from which the sample was taken should be determined. In embodiments involving centralized collection points, the sample domain, from which the sample is chosen, can encompasses a wide geographical area. As stated above, this arrangement prevents having to travel to the remote locations from which the sample domain draws, in order to obtain samples from the area encompassed by the sample domain. A result indicating the presence of a chemical, biological, or radiological agent indicates the presence of undesirable elements somewhere from which the known area the sample domain encompasses. Assuming the materials are brought to the centralized point in a predetermined pattern, the exact location of hot spots can be deduced, e.g., by correlating their position in the collection to location in the pattern or route, or by selecting samples from specific collection points along the route during subsequent collections in that sample domain.

For example, especially in embodiments employing a predetermined traceable route, one can ascertain the location of a hot spot by correlating logistical information between the route and the analyzed sample (e.g., determining where the sample was taken based on the sample lot arrival time). Other, more complex, mathematical models will present themselves to the skilled artisan to provide means to methodically determine the location of a hot spot based on particular factors of the predetermined, traceable route and the sample.

In an embodiment of the present invention, one such mathematical model involves triangulation. The area encompassed by a sample domain can be triangulated. By use of algorithms known in the art, aided by high speed processors, the exact location of a hot spot can be ascertained by inputting logistical information relating to the positive assays for targeted agent(s) using an iterative approach. Various other algorithms will present themselves based on the teachings of various patents and references, including U.S. Pat. Nos. 3,886,553, 4,229,740, and 4,799,062.

Other embodiments of the present invention will utilize current epidemiological tracing techniques to properly analyze positive results for targeted agent(s) so as to determine the location of a hot spot or drop zone. The foundation for these modern epidemiological methods, currently an area of great interest to the scientific community, is found in John Snow's classic studies on the cholera outbreak in nineteenth-century London. See On the Mode of Communication of Cholera, John Snow, 1855.

In other embodiments of the present invention, once a positive result indicates that the particular agent is present in the sample, the surveillance system will report the result. The reporting elicits a response for detection of that agent. For example, the CDC, or local, state, and federal law enforcement authorities can automatically be notified upon the satisfaction of a positive assay protocol for anthrax. It will be understood by the person of ordinary skill, that a suitable particularized response is dependent on the particular agent positively identified in the assay.

Implementing the Surveillance System

It is desirable to regularly test the surveillance system of the present invention. It is not feasible to introduce dangerous materials in order to perform such testing. One aspect of the present invention comprises the development of non-pathogenic models for the surveillance of hazardous materials, e.g. biological agents including *Bacillus anthracis*. As used herein, surveillance for hazardous materials encompasses surveillance for non-pathogenic models employed in lieu of dangerous materials, used for testing purposes.

In embodiments of the present invention, non pathogenic species of *Bacillus*, e.g. *Bacillus globigii*, are used as a model for *Bacillus anthracis* in order to test and optimize the surveillance system of the present invention.

Alternative embodiments of the invention consists of the use of the non-pathogenic *Bacillus thuringiensis* (Bt), including *Bacillus thuringiensis* subsp. *kurstaki* (Bt-01) to serve as a model for *Bacillus anthracis*. Bt is an ubiquitous gram-positive, spore-forming bacterium present in soils throughout the world. Bt produces intracellular protein crystals (cry proteins) that are toxic to a wide number of insect larvae, and is used as a pesticide. Epidemiology studies pursuant to Bt's use as pesticide indicate no danger or adverse effects on the health of humans, sheep, or rats. Thus, unlike other relatives of *Bacillus anthracis*, e.g. *Bacillus cereus* and *Bacillus subtilis*, Bt can be introduced to a sample domain without adverse affects to the population.

In an alternative embodiment of the present invention, a unique UV-resistant strain of *Bacillus thuringiensis* which produces melanin (Bt-m) is used as a surrogate for *Bacillus anthracis*. Bt-m contains two marker genes—the cry and mel gene. Bt-m contains only one cry protein gene as compared to other Bt strains which contain three to four cry protein genes. The cry gene and the mel gene can be identified using specific primers via Real-time PCR. The dark brown pigment produced by Bt-m also provides a unique phenotypic character. Bt-m can be obtained by exposure of Bt-01 to UV at 254 nm and cultivated by fermentation in a laboratory using readily available media, e.g. Brain Heart Infusion (BHI) medium (available from BD, Franklin Lakes, N.J.). The desired size of the Bt-m spores can be obtained using various diluents adhesives and stickers, such as starch, bentonite lactose, casein, etc. See Saxena et al., "A UV tolerant mutant of *Bacillus thuringiensis* subsp. *kurstaki* producing melanin, *Current Microbiology*, 44:25-30 (2002), hereby incorporated by reference.

The Cry marker genes can be identified from extracted DNA by PCR amplification using (SEQ ID NO:1) 5'-GATG-GAGGTAACCCATGGAGGAA-3', and (SEQ ID NO:2) 5'-CTGGAGCTCAMTCMACTAAATTGGATAC-3' primers, and universal (SEQ ID NO:3) 5'-CATGAT-TCATGGGCAGATAAAC-3', and (SEQ ID NO:4) 5'-TTGT-GACACTTCTGCTTCCCATT-3' primers. The Mel marker gene can be identified using (SEQ ID NO:5) 5'-CCGGAAT-TCGTTTAGTACTTTCAGGGGTGTCT-3', and (SEQ ID NO:6) 5'-CCGTGAGCTCCTGCAGTCGCGGATSCG-GTTGTTA-3' primers.

To increase detection ability, Bt-m samples can be enriched by passing them through a series of filtration steps and by heat shock at about 70° C.-80° C. for about 10-20 minutes (to eliminate most of the gram negative bacteria). The surrogate spores can also be made more specific by cloning other genetic markers like green fluorescent protein (GFP) in the Bt strain employed in the testing of the surveillance system of the present invention. The surveillance system of the present invention can be optimized to provide the desired level of identification ease, depending on the goals of the test.

Bt-m can be dispersed in public places in their enriched or pre-enriched state. Bt-m can be dispersed randomly or may be introduced at selective locations. Detection of Bt-m can be carried out using, for example, the above described primers via Real Time PCR. The melanin production by these spores can be determined, for example, by plating the samples on sterile BHI plates.

EXAMPLES

The present invention may be better understood by reference to the following examples, which illustrate the invention but do not limit it.

Example 1

A surveillance system evaluates samples from each of the trucks that conduct the daily collection of debris from city streets using mechanical street sweeper machines. Each morning, approximately 500 sweepers leave from one of over 50 collection stations of the Department of Sanitation of New York City, each sweeper having a specific and pre-planned route for collecting debris, then returning to the station by 11:30 AM to empty the collected refuse. The emptied sweeper collection bins are then rinsed with water sprayers. An aliquot of liquid from this rinsing will contain a sufficient concentration of hazardous materials to allow for their unambiguous detection and identification via DNA or RNA signature sequences. Dispersion patterns are generated from the sweeper's route and by determining concentrations present in more than one sweeper, the location of the epicenter of the attack is estimated from the dispersion patterns. Confirmatory and more detailed sampling follows to target decontamination and biocontainment efforts.

Example 2

The surveillance system conditions of Example 1 are repeated, except samples are taken from liquid portions of the waste collected from the collection of debris from city streets.

Example 3

A surveillance system evaluates samples from each of the trash bins that collect discarded debris from a U.S. Courthouse. According to a pre-determined schedule, trash collecting bins from a particular area are taken to a central point, dumped, and rinsed. After rising, but before being placed back into service, a water sample is taken from the bins, and analyzed for the presence of anthrax. Confirmatory and more detailed sampling follows to target decontamination and biocontainment efforts. Upon the reporting of the presence of anthrax, the surveillance system, which is in communication with the ventilation system, ceases air circulation and dispatches a bio-hazard unit to confirm the presence of a hazardous agent in the courthouse or elsewhere.

Example 4

*Bacillus thuringiensis*, is used a model for *Bacillus anthracis*. The non-pathogenic *Bacillus* genus is disposed throughout a municipality in order to test the early detection and surveillance system. Generally, a few grams of suitable *Bacillus* are placed in various locations within the sample domain, e.g., locations where street sweeper machines clean as part of their regular routes. The technicians carrying out the present invention are not notified of the test, and their response to the "outbreak" is recorded for quality control purposes. Such tests provide for refining sampling, sample preparation, and assaying techniques for anthrax detection according to the present invention.

Example 5

In large metropolitan areas around the country, organizations engage in manual litter removal for urban beautification purposes. Oftentimes, such efforts focus upon the trains, buses, ferries, train stations, subway stations, and other instrumentalities of mass transit. Items collected include cigarette butts, drinking containers, partially-consumed food, personal care products, and other litter that could possibly contain hazardous materials, like hepatitis B and C, or smallpox. These materials are brought to a central area for disposal according to a predetermined schedule. Samples are obtained using swab techniques from these materials, and assayed using RTm-PCR for *Bacillus anthracis*.

Example 6

100 mL of fluid is collected from the chamber of a street sweeper chamber, after making its daily rounds and assayed for *Bacillus anthracis*. Large particles from the fluid are excluded via suction filtration with 1.2 μM pore membrane (Millipore Corp., Billerica, Mass.). The 1.2 μM pore membrane is pasteurized at 70° C. to kill vegetative bacteria. The eluate is passed to another chamber and filtered with a 0.22 μM membrane. The 0.22 μM membrane is rinsed with a sterile physiological saline solution to remove soluble soils, proteins and other contaminants. The resulting filtrate, which contains particles ranging in size from 0.22 to 1.2 μM, are suspended in approximately 1 mL of ¼ strength Ringers solution, and heated to about 70° C. for 10-20 minutes to kill most vegetative bacteria and protozoa cells (Pasteuration). A vital dye such as Crystal Violet or Methylene Blue is added to the 1 mL solution to selectively stain any *Bacillus* spores present in the sample. After 1 minute, the cell suspension is rinsed and suspended in a protozoan culture medium containing a pure culture of approximately $10^{5-6}$ *Tetrahymena pyriformis* protozoa. The *Tetrahymena* are harvested after about 60 minutes, but before 90 minutes of contact with the cell suspension, via centrifugation, filtration, or chemotaxis, and lysed and processed for the extraction of DNA according to parameters established by the Center for Disease Control (see Hoffmaster AF et al., Evaluation and validation of a real-time polymerase chain reaction assay for rapid identification of *Bacillus anthracis*, Emerg Infect Dis., Vol. 8, October 2002.

Example 7

The floors of a train station are regularly cleaned with a mechanical floor-cleaning machine (e.g. a floor buffer, available from Wilkco.com Inc., Casa Grand, Ariz.). The mechanical floor-cleaning machine uses a liquid cleaning solution that recycles through the machine. Prior to disposing the liquid cleaning solution, a sample is collected and analyzed for *Bacillus anthracis* according to the assay technique disclosed in Example 6.

Example 8

*Bacillus thuringiensis* melanin (Bt-m) was isolated after repeated rounds of Bt-01 exposure to UV at 254 nm (See Saxena et al., Current Microbiology 44:25-39 (2002) hereby incorporated by reference). Cells of Bt-m were grown in a rotary shaker at 250 rpm and also a NBS fermentor at 28° C. in Brain Heart Infusion (BHI) medium (BD, Franklin Lakes, N.J.). Spores are released after 48-72 hours, confirmed by microscopic observation. When the sporulation level, i.e. the ratio of the number of colony forming units (CFU) after heat shock (70° C. for 10 minutes) to the number of total viable counts, reaches 90-95%, the biomass is harvested.

Bt-m is isolated from the biomass by precipitation with lactose-acetone, according to the procedure disclosed in Dulmage et al., J. Invertebrate Pathology 15:15-20 (1970), hereby incorporated by reference. Bt-m is also isolated by freeze drying. The purity of the culture can be determined, for example, by microscopic observation and on 12% SDS-PAGE Cry protein assays.

Chromosomal and plasmid DNA is extracted by conventional methods. Amplification of PCR products and identification of their sizes as cry genes is carried out using (SEQ ID NO:1) 5'-GATGGAGGTAACCCATGGAGGAA-3', and (SEQ ID NO:2) 5'-CTGGAGCTCAMTCMACTAAATTG-GATAC-3' primers, and universal (SEQ ID NO:3) 5'-CAT-GATTCATGGGCAGATAAAC-3', and (SEQ ID NO:4) 5'-TTGTGACACTTCTGCTTCCCATT-3' primers. The Melanin gene is identified using (SEQ ID NO:5) 5'-CCG-GAATTCGTTTAGTACTTTCAGGGGTGTCT-3', and (SEQ ID NO:6) 5'-CCGTGAGCTCCTGCAGTGCG-GATSCGGTTGTTA-3' primers. Real time PCR is carried out on a Cepheid SYBR Green PCR kit (Qiagen, Valenica, Calif.)

Example 9

Bt-m obtained by the method described in Example 8 is dispersed in a train station. The brushes of mechanical floor-cleaning machines used to clean the floors of the train selection are washed with water according to their regular maintenance schedule. Custodial crews are not notified of the Bt-m release. Aliquots from the water wash are analyzed for the Cry and Mel marker genes using the techniques disclosed in Example 8.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method of surveillance for the presence of a biological agent, which method comprises: assaying a sample derived from street debris materials collected from a sample domain for the presence of a biological agent comprising the steps of:
   (a) treating the sample to reduce the concentration of bacteria that are preferentially bioencapsulated by *Tetrahymena pyriformis* relative to the bioencapsulation of *Bacillus anthracis*,
   (b) introducing *Tetrahymena pyriformis* to the sample, and
   (c) assaying for *Bacillus anthracis*;
   wherein the sample domain is a route undertaken by a street sweeper machine through a city street and comprises at least one collection point from which the materials are collected from a city street in a pre-existing operation, otherwise unrelated to surveillance.

2. A method of surveillance for the presence of a biological agent, which method comprises:
   (a) treating a sample derived from street debris materials collected from a sample domain to reduce the concentration of bacteria that are preferentially bioencapsulated by *Tetrahymena pyriformis* relative to the bioencapsulation of *Bacillus thuringiensis*, and
   (b) assaying the sample domain for the presence of a biological agent;
   wherein the sample domain is a route undertaken by a street sweeper machine through a city street and comprises at least one collection point from which the materials are collected from a city street in a pre-existing operation, otherwise unrelated to surveillance, wherein the sample is assayed for *Bacillus thuringiensis*.

3. A method of detecting the presence of biological agent which comprises:
   (a) obtaining at least one sample from a collection of street debris that has been exposed to the environment and is collected from a street sweeper machine that follows a pre-defined, traceable route unrelated to surveillance and continuously collects the street debris from an open environment along the pre-defined route;
   (b) treating the sample to reduce the concentration of bacteria that are preferentially bioencapsulated by *Tetrahymena pyriformis* relative to the bioencapsulation of a *Bacillus* spore;
   (c) introducing *Tetrahymena pyriformis* to the sample and assaying the sample for the presence of the *Bacillus* spore;
   (d) determining a result based on the assay; and
   (e) report the result.

4. The method of claim 3, wherein the *Bacillus* spore is *Bacillus anthracis*.

5. The method of claim 3, wherein the *Bacillus* spore is *Bacillus thuringiensis*.

* * * * *